(12) United States Patent
Montet et al.

(10) Patent No.: US 10,005,996 B2
(45) Date of Patent: Jun. 26, 2018

(54) DEVICE FOR THE CULTURING OF MICROORGANISMS AND ASSOCIATED PROCESS

(71) Applicants: BIOMÉRIEUX, Marcy l'Etoile (FR); ARJO WIGGINS FINE PAPERS LIMITED, Manchester (GB)

(72) Inventors: Marie-Pierre Montet, Venissieux (FR); Christine Rozand, St Genis les Ollières (FR); Gael Depres, Chirens (FR); Jean-Marie Vau, Paris (FR); Jean-Marie Baumlin, Anzin Saint Aubin (FR)

(73) Assignees: BIOMERIEUX, Marcy l'Etoile (FR); ARJO WIGGINS FINE PAPERS LIMITED, Manchester (GB)

( * ) Notice: Subject to any disclaimer, the term of this patent is extended or adjusted under 35 U.S.C. 154(b) by 219 days.

(21) Appl. No.: 15/112,988

(22) PCT Filed: Jan. 22, 2015

(86) PCT No.: PCT/EP2015/051295
§ 371 (c)(1),
(2) Date: Jul. 20, 2016

(87) PCT Pub. No.: WO2015/107228
PCT Pub. Date: Jul. 23, 2015

(65) Prior Publication Data
US 2016/0333299 A1    Nov. 17, 2016

(30) Foreign Application Priority Data

Jan. 20, 2014   (FR) .................................... 14 50422

(51) Int. Cl.
| | | |
|---|---|---|
| *C12Q 1/04* | (2006.01) | |
| *C12M 1/36* | (2006.01) | |
| *C12M 1/38* | (2006.01) | |
| *C12M 3/00* | (2006.01) | |
| *C12M 1/34* | (2006.01) | |
| *C12M 1/00* | (2006.01) | |
| *C12M 1/12* | (2006.01) | |
| *G01N 33/52* | (2006.01) | |
| *B05D 1/28* | (2006.01) | |

(52) U.S. Cl.
CPC ............... *C12M 23/20* (2013.01); *B05D 1/28* (2013.01); *C12M 23/04* (2013.01); *C12M 25/14* (2013.01); *C12M 41/36* (2013.01); *C12Q 1/04* (2013.01); *G01N 33/525* (2013.01)

(58) Field of Classification Search
None
See application file for complete search history.

(56) References Cited

U.S. PATENT DOCUMENTS 3,843,452 A  *  10/1974  Freake et al. ........... C12M 23/04
                                                              359/397
2002/0192742 A1    12/2002  Ushiyama et al.

FOREIGN PATENT DOCUMENTS

| EP | 0 242 114 A2 | 10/1987 |
|---|---|---|
| FR | 1 450 149 A | 5/1966 |
| FR | 2 182 073 A1 | 12/1973 |
| FR | 2 766 204 A1 | 1/1999 |
| WO | 96/29427 A1 | 9/1996 |
| WO | 2005/071055 A1 | 8/2005 |

OTHER PUBLICATIONS

Apr. 1, 2015 International Search Report issued in International Patent Application No. PCT/EP2015/051295.
Apr. 1, 2015 Written Opinion of the International Searching Authority issued in International Patent Application No. PCT/EP2015/051295.

* cited by examiner

*Primary Examiner* — Thomas J. Visone
(74) *Attorney, Agent, or Firm* — Oliff PLC

(57) ABSTRACT

A device for the culturing and/or isolation and/or detection and/or identification and/or counting of at least one target microorganism in a sample liable to contain it, which includes a support and a nutrient medium; the support including: a hydrophilic fibrous substrate, at least one porous layer in contact with one of the faces of the fibrous substrate, including a pigment or a mixture of pigments and at least one binder, the pigment having a size of less than 5 μm and the amount of the pigment or the mixture of pigments being between 50 and 97% by dry weight, with respect to the dry weight of the porous layer; the nutrient medium being included in the fibrous substrate. Also relates to the use and to the process for the manufacture of the device.

17 Claims, No Drawings

DEVICE FOR THE CULTURING OF MICROORGANISMS AND ASSOCIATED PROCESS

The present invention relates, generally, to the field of in vitro diagnosis and more specifically to the field of microbiological diagnosis. More particularly, it relates to a device for the culturing of microorganisms resulting from a contaminated sample.

In the fields of clinical diagnosis and industrial, food-processing, pharmaceutical or cosmetic microbiological control, gelled culture media in petri dishes, generally agar culture media, have formed an essential tool in the detection and identification of pathogenic microorganisms since the end of the 19$^{th}$ century.

Agar media for the growth of microorganisms are very widespread. Nevertheless, their preparation is time consuming as they have to be prepared immediately before they are used in order to ensure that they are sterile.

There also exist pre-prepared agars. The latter are expensive and have a short shelf life.

Several products have been provided commercially for replacing a petri dish culture medium. Thus, 3M provides the Petrifilm™ system, which is composed of two parts, a lower film and an upper film which are covered at the surface with certain components of the dehydrated culture medium. At the time of the analysis, the sample is deposited between these two films.

Another system developed by Nissui Pharmaceutical, Compact Dry™, also consists of a dehydrated medium.

These culture media have the advantage that they can be stored for longer than a ready-to-use agar culture medium. They can also be compact and thus use a small incubation space.

Nevertheless, these culture media do not make it possible to isolate microorganisms by rubbing a mechanical means over the medium.

Specifically, the isolation of microorganisms on a gelled culture medium, from a sample to be analyzed or from a suspension of microorganisms, is a stage which is often essential to many methods of microbiological analysis. This stage is in particular used to carry out identifications, to confirm the microbial purity of a sample or also to carry out a bacterial count by counting the isolated colonies thus obtained.

The isolation techniques have the objective of obtaining, at the surface of a gelled nutritive medium, colonies which can be used directly (DUCs) to identify and determine the sensitivity to antibiotics. They are well known to a person skilled in the art, the streaking (or quadrant) technique being the reference technique. The latter consists in depositing the inoculum by rubbing over a surface with an equal probability per unit of surface area traveled. The local density distributed decreases approximately exponentially during the travel of the instrument. Thus, several areas of plating out starting from a single inoculum are produced, with or without overlapping of the areas, in order to obtain the appropriate distribution effect and depletion of bacteria when it comes to the subsequent plating-out segment. At the end of plating out, the cells are sufficiently isolated from one another for the microbial growth in DUC form (visible colonies or microcolonies) not to be even partially superimposed. This technique can also be carried out by a single continuous inoculation in a spiral by means of a rotating plate or by a magnetic bead driven by a device producing continuous inoculation which is not overlapping or optionally is partially overlapping.

Another widespread technique consists of the isolation on a dish of gelled medium by surface plating out. In this case, a mixture of cells at a low cell concentration making it possible to culture from 30 to 300 cells is plated out at the surface of the gel of a petri dish with a diameter of 9 cm, each cell developing into an isolated colony. When fewer than 30 cells are brought into contact with the nutritive gel, statistical problems distort the accuracy of the count. When the number counted is above 300 cells, counting errors appear because of overlapping of the surfaces of the colonies. The plating out is usually performed with an instrument comprising, for example, a linear part which is in contact with the gel or using beads with a diameter of a few millimeters, which roll randomly on the surface via an uncoordinated movement. This technique is suitable only for a weakly contaminated or diluted sample since a high number of cells increases the probability of confluence of the colonies resulting from the growth.

It is also possible to perform an isolation on a dish by deep inoculation. The starting sample is diluted several times so as to sufficiently reduce the microbial population and to obtain separate colonies. Small volumes of each of the diluted samples are then mixed with a liquid gel, usually agar kept molten approximately at 45° C. The mixtures are immediately poured into sterile culture dishes and, after gelling and incubation, each cell is immobilized and forms a colony.

Certain manual methods have been automated by virtue of the development of devices.

This is the subject matter, for example, of the document EP-0 242 114, which describes a device and a method for the inoculation of a culture medium with a sample. The method consists in producing several plating-out segments from an inoculum. These segments are in the form of arcs of a circle and are produced by means of four different plating-out heads. An effect of dilution of the sample is obtained by partial overlapping of the subsequent segments. The method described in the document is in fact very similar to the reference manual isolation method.

More recently, novel isolation methods have been developed, making it possible to improve the bacterial exhaustion by the use of an optimized applicator, such as described in the document WO-A-2005071055. This is the case in particular of the inoculation method employed in the automatic device sold by the applicant company bioMérieux under reference PREVI™ Isola.

Nevertheless, these isolation techniques are effective only on gelled culture media.

This is because isolation on non-agar systems, such as Petrifilm™, exhibits a number of disadvantages. The isolation of colonies on these media is only possible by inclusion in the gel formed during rehydration and thus starting from a starting sample with a low level of contamination or which has been subjected to a series of dilutions. The final concentration, to be deposited on the medium, has to be less than 300 cfu/ml (Colony Forming Unit), these conventional data depending on the size of the colony.

Furthermore, these media cannot be subjected to the mechanical stress of a means of isolation by exhaustion without being damaged. Thus, one of the major problems of these rehydratable culture media is that they are not compatible with manual or automated mechanical isolation of microorganisms. They require, when the starting sample is heavily contaminated (above 300 Colony Forming Units/ml), a series of dilutions to be carried out, involving a larger test sample, a loss of time and the consumption of a large number of reagents (culture medium, tubes of diluents, and the like), generating a large volume of waste (autoclaving, cost of the treatment).

Furthermore, if a large number of dilutions is carried out, there is a risk of losing, by the effect of the diluting, the target pathogenic microorganism, if the latter is present in a small amount with respect to the total microflora.

In the same way, the addition of a filtering membrane to an agar medium is known from the prior art. Thus, for the counting of bacteria in water, a filtering membrane is used in order to collect the microorganisms at its surface. This membrane is subsequently placed on an agar. The filtering membrane allows the nutrient from the agar to pass through it in order to bring about the growth of the microorganisms in the form of colonies on its surface.

Alternatively, the membrane can be placed on an absorbent fibrous material containing dehydrated nutrient which is moistened with a predetermined amount of water.

These membranes are produced by plastic film perforation techniques, such as by laser or electron beams, or by assembling fibers, to perform the role of filtration.

Mention may be made, for example, of the Sartorius microfilters consisting of a plastic composed of a polymeric network exhibiting different pore sizes. These systems exhibit in particular the disadvantage of instability, it being possible for the membrane deposited on the culture medium to exhibit deformations and creases. The transfer and the handling of the membrane are not easy and are a risk of contamination. Furthermore, neither do these systems make possible the isolation by contact with an isolation means as a result of the weakness of the membrane.

The document FR 2 182 073 provides a device comprising a microporous membrane used in combination, via a continuous interfacial area, with an absorbent layer.

This structure has three layers, which has the disadvantage of distancing the nutrients from the actual growing area.

In view of all the problems expanded upon above, the present invention provides a novel device for the culturing of microorganisms.

Thus, one objective of the present invention is to provide a robust device and a robust process which make possible the growth of microorganisms.

One objective of the invention is also to make possible the isolation of microorganisms on a rehydratable culture medium, or a culture medium rehydrated slightly before or simultaneously with the microbial isolation.

Another objective of the present invention is to provide a process for the isolation of microorganisms starting from a sample having a high initial microbial concentration.

ACCOUNT OF THE INVENTION

These objectives, among others, are achieved by the present invention, which provides a device for the culturing and/or isolation and/or detection and/or identification and/or counting of at least one target microorganism in a sample liable to contain it, characterized in that it comprises a support and a nutrient medium; said support comprising:
  a hydrophilic fibrous substrate,
    at least one porous layer in contact with one of the faces of the fibrous substrate, comprising a pigment or a mixture of pigments and at least one binder, said pigment having a size of less than 5 µm and the amount of said pigment or said mixture of pigments being between 50 and 97% by dry weight, with respect to the dry weight of the porous layer;
  said nutrient medium being included in the fibrous substrate.

The term "fibrous substrate" is understood to mean more or less intertwined, contiguous, small-sized fibers constituting an assembly which has a mechanical integrity and which can be traversed by a liquid. Preferably, the fibrous substrate comprises cellulose fibers, in particular cotton fibers.

The fibrous substrate must be hydrophilic in order for it to be able to absorb an aqueous solution of a nutrient medium and to uniformly supply its surface. The fibrous substrate can act as nutrient medium reservoir. The fibrous substrate must be sufficiently hydrophilic and absorbent for the surface of the system to rapidly moisten when the fibrous substrate is brought into contact with a liquid medium.

Advantageously, the nutrient medium included in the fibrous substrate is dehydrated.

Thus, the device according to the invention exhibits the advantage of having a greater lifetime than the pre-prepared agar. It can also be irradiated in order to be sterilized.

The role of the porous layer is to retain the microorganisms at its surface while allowing the water laden with nutrient included in the fibrous substrate to nourish these microorganisms. Thus, the porous layer comprises a pigment or a mixture of pigments, said pigment having a size of less than 5 µm and the amount of said pigment or of the mixture of pigments being between 50 and 97% by dry weight, with respect to the dry weight of the porous layer.

The pigments, by their nature, their size and their steric arrangement in the porous layer, will then prevent the microorganisms from migrating from the surface toward the fibrous substrate while being permeable to the components included in the fibrous substrate located under this layer.

Preferably, the layer has pores of less than 600 nm, preferably of less than 400 nm. It also has sufficient tortuosities for the microorganisms not to be able to pass through it.

The choice of the pigments and the amount of the latter on the surface of the fibrous substrate also prevent the liquid from being free at the surface of the porous layer, which would result in the growth of star-shaped colonies.

Preferably, the porous layer is integral with one of the faces of the fibrous substrate. Thus, the porous layer and the substrate form a whole and cannot be separated from one another without damaging one and/or the other.

The term "pigments" is understood to mean solid compounds, normally insoluble in water (with the exception of $CaCO_3$, which is a pigment soluble in acidic water), of small sizes typically of between 0.1 and 5 µm, the size, the shape and the size distribution of which depend on the chemical nature, the origin and the method of manufacture. Usually, organic pigments are distinguished from inorganic pigments. The organic pigments are plastic pigments in the form of solid or hollow beads.

By way of example, the inorganic pigments can be chosen from the following pigments: ground calcium carbonates, precipitated calcium carbonates, kaolin, silica, talc, zinc oxide, barium sulfate or titanium dioxide.

Preferably, the pigments are inorganic pigments chosen from the following pigments: kaolin, talc, titanium dioxide or calcium carbonate.

The amount of said pigment or of the mixture of pigments is between 50 and 97% by dry weight, with respect to the dry weight of the porous layer, preferably between 60 and 95% and more preferably between 80 and 90%.

At least one of the pigments has a size of less than 5 micrometers, preferably of less than 3 micrometers and more preferably still of less than 2 micrometers.

During their depositions, the pigments get caught on one another, leaving room for open pores between them, the size of the pores depending mainly on the shape of the pigments, on their mean size and on their size distribution.

Thus, the shape of the pigments affects the volume of the pores. In theory, perfectly cubic pigments having the same dimension could be put together without leaving a space between them. In the case of spheres of the same size, if they are assembled as close together as possible, 26% of the space is occupied by the interstices. Likewise, if the solid particles are composed of large and small pigments, the small pigments could become lodged between the large pigments, thus filling the volume of the interstices and reducing the volume of the pores. The size of the interstices between the pigments is typically smaller than the pigments themselves. Thus, by using fine pigments, pores having smaller sizes than by using coarse pigments are created. It is then possible, depending on the type of microorganism targeted, to choose a mean porosity of the layer which is higher or lower, such as, for example, a mean porosity of greater than 1 micron for the growth of yeast.

Furthermore, the pigments can join together in a more or less compact manner. In the same way that a box containing grains is shaken in order to compact them, the more or less rapid drying of the layer can influence the arrangement of the pigments with respect to one another in their consolidation phase and can modify the pore volume.

The pigments are bonded together using a binder, such as, for example, styrene-butadiene latex, styrene-acrylic latex, carboxymethyl cellulose, polyvinyl alcohol, starch or gelatin. Preferably, the binder is styrene-butadiene latex and/or styrene-acrylic latex and/or carboxymethyl cellulose.

The amount of binder can also adjust the porosity of the layer. Thus, if a layer is composed of pigment and saturated with binder, the binder fills in the interstices between the solid pigments and can then constitute a solid and sturdy compact assembly, once dried. When the amount of binder is low with respect to the pigment, hollows are created between the pigments which the binder, in a low amount, cannot completely fill in. These combined hollows constitute an interstitial porosity which can be characterized, inter alia, by the dimension of these pores and by the combined volume of the pores. Thus, when the amount of binder is low with respect to the pigment of the layer, it provides a degree of interstitial porosity between the pigments.

Preferably, the amount of binder is between 3 and 25% by dry weight, with respect to the dry weight of the porous layer, preferably between 5 and 15%.

Preferably, the amount of pigments and/or of binders is between 30 g/m$^2$ and 90 g/m$^2$, preferably between 50 g/m$^2$ and 80 g/m$^2$.

Other components can be added to the porous layer, such as a crosslinking agent, a thickener, an antifoaming agent or a surfactant. These components are appropriate to the coating process.

Advantageously, the device according to the invention makes possible isolation of the microorganisms.

Isolation of microorganisms can be carried out using a mechanical means in contact with the device, such as a loop, which requires continuous sliding of the loop over the surface of the device, namely the porous layer. In this case, in order to prevent the plating-out means from detaching the porous layer, it is necessary to use a binder and a crosslinking agent in the layer. The crosslinking agent crosslinks the binders and prevents the layer from disintegrating when it is wet. Thus, according to a specific form of the invention, the porous layer comprises a crosslinking agent. Mention may be made, among the crosslinking agents which can be used, of: isocyanate, carbodiimide acetaldehyde, polyvalent salts, zirconium salts, epoxy compounds, bifunctional epoxy compounds, maleic anhydride, vinylformamide copolymer, ethanediol-based copolymer, synthetic tannins, aqueous polyurethane dispersions, cyclodextrin, phosphorus oxychloride, sodium trimetaphosphate, modified glyoxals, polyamidoamine-epichlorohydrin and melamine-formaldehyde. Preferably, the crosslinking agent is chosen from the following crosslinking agents: isocyanate and melamine-formaldehyde.

The inventors have shown that particularly effective sliding actions were obtained when the porous layer comprises kaolin or talc.

Thus, the rubbing of the loop is lower over a surface produced with a layer of kaolin than with the other pigments. For this reason, isolation is facilitated. The smooth surface of the kaolin layer, the pigments of which have the platelet shape, is appropriate to the isolation carried out using an isolation means in contact with the device. Furthermore, kaolin is an aluminosilicate which is rather neutral for biological applications. In a specific embodiment, the kaolin is then used in association with styrene-butadiene as binder and with isocyanate as crosslinking agent.

According to a preferred embodiment, the porous layer is opaque in order not to allow light resulting from the fibrous material to pass. This is because this would have the disadvantage of interfering with the view of the colonies. Advantageously, the device comprises a first porous layer, in contact with the fibrous substrate, comprising titanium dioxide and a second external porous layer comprising kaolin. The titanium dioxide layer thus prevents the light resulting from the fibrous substrate from passing and makes possible better visualization of the colonies, without preventing the growth of the colonies.

In the same way, in order to improve the contrast of the colonies, the color of the porous membrane will be adjusted according to the visualization and lighting means. For example, the porous layer will be white with CIE Whiteness of greater than 65 for visualization with the naked eye with frontal lighting. The fibrous substrate and white porous layer combination has a better contrast and thus a better identification of the target microorganism than an agar.

In addition, the device according to the invention exhibits several ecological advantages:
  it does not require agar, which is a limited resource;
  it can be destroyed by combustion with very little energy and without release of toxic matter. It is thus easy and inexpensive to destroy and it can be destroyed close to the site of the analysis, which is advantageous for a contaminated material.
  the fibrous substrate and pigmentary porous layer combination can be produced at more than 95%, with renewable materials.

The invention also relates to a process for the manufacture of a support comprising a stage of deposition by coating, on one of the faces of a fibrous substrate, of a porous layer comprising a pigment or a mixture of pigments and at least one binder, said pigment having a size of less than 5 μm and the amount of said pigment or of the mixture of pigments being between 50 and 97% by dry weight, with respect to the dry weight of the porous layer.

The porous layer can be deposited by coating techniques, namely transfer, rolling, dry coating or wet coating techniques. The wet coating techniques include in particular curtain, meniscus, slot, photogravure, reverse gravure, size press, Mayer bar, knife and air knife coating. The wet layer is subsequently dried by air or by radiative techniques, such as infrared rays or microwaves.

Thus, the layer and the fibrous substrate are integral. They form a whole and cannot be separated without there being damage to the substrate and/or to the layer.

A calendering stage can also be carried out before and/or after the coating.

The invention also relates to the product obtained by this process. This product corresponds to a process for the manufacture of an intermediate product in which the fibrous substrate does not comprise nutrient medium.

The invention also relates to a support intended for the growth of microorganisms comprising:
- a hydrophilic fibrous substrate;
- at least one porous layer deposited on one of the faces of the fibrous substrate, comprising a pigment or a mixture of pigments and at least one binder, said pigment having a size of less than 5 µm and the amount of said pigment or of the mixture of pigments being between 50 and 97% by dry weight, with respect to the dry weight of the porous layer.

Preferably, the fibrous substrate comprises cellulose fibers, in particular cotton fibers.

More preferably, the pigments are inorganic pigments chosen from the following pigments: kaolin, talc, titanium dioxide or calcium carbonate.

Advantageously, the amount of said pigment or the mixture of pigments is between 50 and 97% by dry weight, with respect to the dry weight of the porous layer, preferably between 60 and 95% and more preferably between 80 and 90%.

Preferably, the binder is styrene-butadiene latex and/or styrene-acrylic latex and/or carboxymethyl cellulose and the crosslinking agent is chosen from the following crosslinking agents: isocyanate and melamine-formaldehyde.

In a specific embodiment, the kaolin is used in combination with styrene-butadiene as binder and with isocyanate as crosslinking agent.

In another specific embodiment, the device comprises a first porous layer, in contact with the fibrous substrate, comprising titanium dioxide and a second external porous layer comprising kaolin.

The invention also relates to a process for the manufacture of a device according to the invention comprising a stage, prior or subsequent to the coating stage, of bringing the hydrophilic fibrous substrate into contact with a nutrient medium.

The invention also relates to the product obtained by this process.

The fibrous substrate can be impregnated with a dehydrated or liquid nutrient medium.

When, before being impregnated with the nutrient medium, the fibrous substrate is already covered with a porous layer, impregnation takes place via the surface of the fibrous substrate devoid of porous layer. The impregnation is then facilitated and does not damage the properties of the porous layer.

The impregnation by a dehydrated medium can be carried out according to the method described in the patent application FR 1 450 149. When the fibrous substrate is impregnated with a liquid or semiliquid medium, it can be dried in order to provide a device according to the invention with a dehydrated medium.

The invention also relates to the use of a device according to the invention for culturing and/or isolating and/or detecting and/or identifying and/or counting at least one target microorganism, preferably at least one target bacterium, in a sample liable to contain it.

Advantageously, the device is used to culture and isolate at least one target microorganism, preferably at least one target bacterium, in a sample liable to contain it.

Preferably, it comprises a crosslinking agent in the porous layer, preferably chosen from isocyanate and melamine-formaldehyde. Advantageously, kaolin is used in combination with styrene-butadiene as binder and with isocyanate as crosslinking agent. In another specific embodiment, the device comprises a first porous layer, in contact with the fibrous substrate, comprising titanium dioxide and a second external porous layer comprising kaolin.

The invention provides a process for the culturing and/or isolation and/or detection and/or identification and/or counting of at least one target microorganism, in a sample liable to contain it, said process comprising the following stages:
a) providing a device as claimed in any one of claims 1 to 10,
b) depositing a predetermined volume of the sample on the porous layer,
c) incubating the device for a predetermined time and at a predetermined temperature which make possible the growth and the appearance of colonies of at least one target microorganism,
d) detecting and/or identifying and/or counting the colonies formed;

said process also comprising at least one stage of rehydration of the culture medium with a predetermined volume of liquid, before or simultaneously with stage b) and/or c).

The rehydration is carried out via the surface of the fibrous substrate devoid of porous layer.

Advantageously, the process is characterized in that a device comprising a crosslinking agent is provided and that, after deposition of the sample, the microorganisms are isolated using an isolation means. The microorganisms are isolated by exhaustion or by covering of the sample.

Thus, the process according to the invention exhibits the advantage of making possible the isolation of microorganisms using an isolation means such as is possible to do it on an agar medium.

The term "sample" is understood to mean a small part or small amount separated from an entity by a subtractive act, normally sampling, for analytical purposes. The sample can be of biological, human, animal, vegetable or environmental origin. It may relate to a product during an industrial process or a finished product, for example a foodstuff. It can thus correspond to a sampling of biological fluid (total blood, serum, plasma, urine, cerebrospinal fluid, organic secretion), a tissue sampling or isolated cells. It can be of industrial origin, i.e., according to a nonexhaustive list, a sampling of air, a sampling of water, a sampling carried out on a surface, a part or a product in the course of treatment or manufactured, or a product of food origin. Mention may be made, among the samples of food origin, nonexhaustively, of a sample of milk products (yogurts, cheeses, and the like), of meat, of fish, of eggs, of fruit, of vegetables, of water, of drink (milk, fruit juice, soda, and the like) and the constituent or ancillary products of the finished product. Finally, a food sample can result from a feed intended for animals, such as in particular animal meals. This sampling product can be subjected, prior to its analysis, to a preparation of enrichment, extraction, concentration or purification type, according to methods known to a person skilled in the art.

According to a preferred embodiment, the volume of sample deposited on the culture medium is between 10 and 1000 µl.

Within the meaning of the present invention, the term "microorganism" covers gram-positive or gram-negative bacteria, yeasts, molds, amebae and more generally unicellular organisms, invisible to the naked eye, which can be handled and multiplied in a laboratory.

According to a preferred embodiment of the invention, the microorganism is a gram-negative or gram-positive bacterium or a yeast.

Mention may be made, as gram-positive bacteria, of bacteria of the following genera: *Enterococcus, Streptococcus, Lactobacillus, Bifidobacterium, Staphylococcus, Bacillus, Listeria, Clostridium, Mycobacteria, Nocardia, Corynebacteria, Micrococcus* and *Deinococcus*.

Mention may be made, as yeasts, of yeasts of the following genera: *Candida, Cryptococcus, Saccharomyces* and *Trichosporon*.

Mention may be made, as molds, of molds of the following genera: *Aspergillus, Penicillium* and *Cladosporium*.

Mention may be made, as gram-negative bacteria, of bacteria of the following genera: *Salmonella, Escherichia coli* and *Pseudomonas*.

The term "nutrient medium" is understood to mean a medium comprising all the components necessary for the survival and/or for the growth of the microorganisms. The medium according to the invention can comprise, for example: peptones, one or more growth factors, hydrocarbons, one or more selective agents, buffers, one or more gelling agents, and the like. Generally, the medium can in addition contain a substrate which makes possible the detection of an enzymatic or metabolic activity of the target microorganisms by virtue of a signal which can be detected directly or indirectly. This substrate can be bonded to a part acting as fluorescent or chromogenic label. Mention may be made, as an example of chromophore, of neutral red, aniline blue or bromocresol blue.

The detection of the bacteria makes it possible to reveal, to the naked eye or using an optical device, the existence of growth of the target bacteria, namely the appearance of colored and/or fluorescent colonies (according to whether a chromogenic substrate, a fluorogenic substrate or a substrate exhibiting both characteristics simultaneously is used).

As indicated above, the detection of the fluorescence emitted after cleaving of the fluorogenic enzymatic substrates requires resorting to an optical device, whereas the visualization of the cleaving of the chromogenic enzymatic substrates can be carried out with the naked eye or, if need be, using an optical device.

Advantageously, the detection of the bacteria also makes it possible to identify them and/or to count them.

Preferably, the identification takes place by spectral analysis.

The counting of the bacteria consists, for its part, in quantifying the number of colonies of bacteria which have grown over the culture medium by employing microbiological techniques well known to a person skilled in the art.

The invention, its functionality, its applications and its advantages will be better understood on reading the following description comprising several comparative examples, in which:

The layer T is an aqueous solution composed of 1 part of carboxymethyl cellulose, 5 parts of styrene-butadiene latex and 0.5 part of acrylate polymer dispersing agent per 100 parts of titanium dioxide pigments (Tiona AT1).

The layer PU is an aqueous solution composed of one part of carboxymethyl cellulose, 12 parts of styrene-butadiene latex, 100 parts of polyurethane beads (Decosoft 7D, Microchem, Erlenbach, Switzerland), 1 part of acrylate polymer dispersing agent, 1 part of antifoaming agent and 0.9 part of isocyanate crosslinking agent.

The layer K1 is an aqueous solution composed of one part of carboxymethyl cellulose, 12 parts of styrene-butadiene latex, 100 parts of kaolin pigment (Capim RG Imerys Rio Capim Caulim), 1 part of antifoaming agent and 0.9 part of isocyanate crosslinking agent.

The layer K2 is an aqueous solution composed of one part of carboxymethyl cellulose, 20 parts of styrene-butadiene latex, 100 parts of kaolin pigment (Capim RG Imerys Rio Capim Caulim) and 1.5 part of isocyanate crosslinking agent.

EXAMPLE 1

Fibrous substrate not covered with a porous layer.

A fibrous substrate manufactured by Arjowiggins Creative Papers of 400 $g/m^2$, consisting of cotton fibers manufactured on a paper machine, is sterilized, placed in a petri dish and impregnated with nutrients (Chrom ID™ CPS 3 medium) (bioMérieux Ref 43541) on the face of the fibrous substrate devoid of the porous layer. An inoculum containing the bacterium *Escherichia coli* is applied with a loop according to the quadrant method. The assembly is placed in an oven at 37° C. for 24 h.

Bacterial growth is observed within the fibrous material. It is not possible to identify or to count colonies.

EXAMPLE 2

Fibrous substrate covered with a layer composed of polyurethane beads with a size of between 6 and 9 micrometers.

A fibrous substrate manufactured by Arjowiggins Creative Papers of 400 $g/m^2$, consisting of cotton fibers manufactured on a paper machine, is coated with a Mayer bar with 30 $g/m^2$ dry of layer T and then 20 $g/m^2$ dry of layer PU. The assembly is sterilized, placed in a petri dish and impregnated with nutrients (Chrom ID CPS 3 medium) (bioMérieux Ref 43541) on the face of the fibrous substrate devoid of the porous layer. With regard to one sample, an inoculum containing the bacterium *Escherichia coli* is applied with a loop according to the quadrant method and, with regard to another sample, an inoculum containing the bacterium *Escherichia coli* is diluted and spread with a scraper over the surface of the product. The inoculum is deposited on the porous layer.

The samples are placed in an oven at 37° C. for 24 h.

The colonies grow deeply and are not truly identifiable on the isolation sample.

There are no isolated colonies on the enumeration sample.

EXAMPLE 3

Fibrous substrate with a layer in contact with the substrate containing titanium dioxide and a surface layer containing kaolin.

A fibrous substrate manufactured by Arjowiggins Creative Papers of 400 $g/m^2$, consisting of cotton fibers manufactured on a paper machine, is coated with a Mayer bar with 30 $g/m^2$ dry of layer T and then 20 $g/m^2$ dry of layer K1. The assembly is sterilized, placed in a petri dish and impregnated with nutrients (Chrom ID CPS 3 medium) (bioMérieux Ref 43541) on the face of the fibrous substrate devoid of the porous layer.

The inoculum is deposited on the porous layer: With regard to a sample 3A, an inoculum containing the bacterium *Enterococcus faecalis* is diluted and spread with a scraper over the surface of the product.

With regard to a sample 3B, an inoculum containing the bacterium *Citrobacter freundii* is diluted and spread with a scraper over the surface of the product.

With regard to a sample 3C, an inoculum containing the bacterium *Serratia marcescens* is diluted and spread with a scraper over the surface of the product.

With regard to a sample 3D, an inoculum containing the bacterium *Escherichia coli* is applied with a loop according to the quadrant method.

With regard to a sample 3E, an inoculum containing the bacterium *Staphylococcus aureus* is applied with a loop according to the quadrant method.

With regard to a sample 3F, an inoculum containing the bacterium *Klebsiella pneumoniae* is applied with a loop according to the quadrant method.

With regard to a sample 3G, an inoculum containing the bacterium *Pseudomonas aeruginosa* is applied with a loop according to the quadrant method.

With regard to a sample 3H, an inoculum containing the bacterium *Enterobacter cloacae* is applied with a loop according to the quadrant method.

With regard to a sample 3I, an inoculum containing the bacterium *Acinetobacter baumanii* is applied with a loop according to the quadrant method.

The samples are placed in an oven at 37° C. for 24 h.

The wet CIE whiteness of the product is 68.

The colonies of the enumeration samples 3A, 3B and 3C are very round and isolated and can be counted.

The colonies on the isolation samples 3D, 3E, 3F, 3G, 3H and 3I are very round and isolated; the morphotype is adhered to.

EXAMPLE 4

Fibrous substrate with a bottom layer containing titanium dioxide and a top layer containing kaolin applied by 3 successive coatings.

A fibrous substrate manufactured by Arjowiggins Creative Papers of 400 g/m$^2$, consisting of cotton fibers manufactured on a paper machine, is coated with a Mayer bar with 30 g/m$^2$ dry of layer T and then three times 20 g/m$^2$ dry of layer K1. The assembly is sterilized, placed in a petri dish and impregnated with nutrients (Chrom ID CPS 3 medium) (bioMérieux Ref 43541) on the face of the fibrous substrate devoid of the porous layer.

The inoculum is deposited on the porous layer:

An inoculum containing the bacterium *Escherichia coli* is applied with a loop according to the quadrant method. The sample is placed in an oven at 37° C. for 24 h.

The colonies are very round and isolated.

EXAMPLE 5

Fibrous substrate coated and impregnated with a water-soluble polymer in order to thicken the nutrient in order to reduce the lateral movements of the liquid within the substrate.

A fibrous substrate manufactured by Arjowiggins Creative Papers of 400 g/m$^2$, consisting of cotton fibers manufactured on a paper machine, is impregnated with 30 g/m$^2$ dry of hydroxyethyl cellulose (Cellosize WP 09L) and coated with a Mayer bar with 30 g/m$^2$ dry of layer T and then 20 g/m$^2$ dry of layer K1. The assembly is sterilized, placed in a petri dish and impregnated with nutrients (Chrom ID CPS 3 medium) (bioMérieux Ref 43541) on the face of the fibrous substrate devoid of the porous layer.

The inoculum is deposited on the porous layer:

With regard to a sample 5A, an inoculum containing the bacterium *Escherichia coli* is applied with a loop according to the quadrant method.

With regard to a sample 5B, an inoculum containing the bacterium *Escherichia coli* is diluted and spread with a scraper over the surface of the product.

With regard to a sample 5C, an inoculum containing the bacterium *Enterococcus faecalis* is diluted and spread with a scraper over the surface of the product.

With regard to a sample 5D, an inoculum containing the bacterium *Serratia marcescens* is diluted and spread with a scraper over the surface of the product.

With regard to a sample 5E, an inoculum containing the bacterium *Citrobacter freundii* is diluted and spread with a scraper over the surface of the product.

The samples are placed in an oven at 37° C. for 24 h.

The colonies on the isolation sample 5A are very round and isolated.

The colonies of the enumeration samples 5B, 5C, 5D and 5E are very round and isolated and can be counted; the morphotype is adhered to.

EXAMPLE 6

Fibrous substrate covered with a single layer consisting of kaolin.

A fibrous substrate manufactured by Arjowiggins Creative Papers of 400 g/m$^2$, consisting of cotton fibers manufactured on a paper machine, is coated with a Mayer bar with 26 g/m$^2$ dry of layer K2. The assembly is sterilized, placed in a petri dish and impregnated with nutrients (Chrom ID CPS 3 medium) (bioMérieux Ref 43541) on the face of the fibrous substrate devoid of the porous layer.

The inoculum is deposited on the porous layer:

With regard to a sample 6A, an inoculum containing the bacterium *Escherichia coli* is applied with a loop according to the quadrant method.

With regard to a sample 6B, an inoculum containing the bacterium *Escherichia coli* is diluted and spread with a scraper over the surface of the product.

The samples are placed in an oven at 37° C. for 24 h.

The colonies on the isolation sample 6A are round and isolated.

The colonies of the enumeration sample 6B are round and isolated and can be counted.

The invention claimed is:

1. A device for the culturing and/or isolation and/or detection and/or identification and/or counting of at least one target microorganism in a sample liable to contain it, wherein it comprises a support and a nutrient medium;
   said support comprising:
   a hydrophilic fibrous substrate,
   at least one porous layer in contact with one of the faces of the fibrous substrate, comprising a pigment or a mixture of pigments and at least one binder, said pigment having a size of less than 5 μm and the amount of said pigment or said mixture of pigments being between 50 and 97% by dry weight, with respect to the dry weight of the porous layer;
   said nutrient medium being included in the fibrous substrate.

2. The device as claimed in claim 1, wherein the porous layer is integral with one of the faces of the fibrous substrate.

3. The device as claimed in claim 1, wherein the pigments are inorganic pigments chosen from the following pigments: kaolin, talc, titanium dioxide and calcium carbonate.

4. The device as claimed in claim 1, wherein the binder is chosen from the following binders: styrene-butadiene latex, styrene-acrylic latex and carboxymethyl cellulose.

5. The device as claimed in claim 1, wherein the amount of binder is between 3 and 25% by dry weight, with respect to the dry weight of the porous layer.

6. The device as claimed in claim 1, comprising:
   a first porous layer, in contact with the fibrous substrate, containing titanium dioxide, and
   a second external porous layer comprising kaolin.

7. The device as claimed in claim 1, wherein the fibrous substrate comprises cellulose fibers.

8. The device as claimed in claim 1, wherein the nutrient medium is a dehydrated medium.

9. The device as claimed in claim 1, wherein the porous layer comprises a crosslinking agent.

10. The device as claimed in claim 9, wherein the crosslinking agent is chosen from the following crosslinking agents: isocyanate and melamine-formaldehyde.

11. A process for the manufacture of a support comprising a stage of deposition by coating, on one of the faces of a hydrophilic fibrous substrate, of a porous layer comprising a pigment or a mixture of pigments and at least one binder, said pigment having a size of less than 5 µm and the amount of said pigment or of the mixture of pigments being between 50 and 97% by dry weight, with respect to the dry weight of the porous layer.

12. The process for the manufacture of a device as claimed in claim 11, comprising a stage, prior or subsequent to the coating stage, of bringing the hydrophilic fibrous substrate into contact with a nutrient medium.

13. A product obtained by the process as claimed in claim 11.

14. A support intended for the growth of microorganisms comprising:
   a hydrophilic fibrous substrate;
   at least one porous layer deposited on one of the faces of the fibrous substrate, comprising a pigment or a mixture of pigments and at least one binder, said pigment having a size of less than 5 µm and the amount of said pigment or of the mixture of pigments being between 50 and 97% by dry weight, with respect to the dry weight of the porous layer.

15. A process for the culturing and/or isolation and/or detection and/or identification and/or counting of at least one target microorganism, in a sample liable to contain it, said process comprising the following stages:
   a) providing a device as claimed in claim 1,
   b) depositing a predetermined volume of the sample on the porous layer,
   c) incubating the device for a predetermined time and at a predetermined temperature which make possible the growth and the appearance of colonies of at least one target microorganism,
   d) detecting and/or identifying and/or counting the colonies formed;
   said process also comprising at least one stage of rehydration of the culture medium with a predetermined volume of liquid, before or simultaneously with stage b) and/or c).

16. The process as claimed in claim 15, wherein a device, in which the porous layer comprises a crosslinking agent, is provided and that, after the deposition of the sample, the microorganisms are isolated using an isolation means.

17. The process as claimed in claim 15, wherein the identification takes place by spectral analysis.

* * * * *